(12) United States Patent
Rashid

(10) Patent No.: US 6,200,600 B1
(45) Date of Patent: Mar. 13, 2001

(54) CONTROLLED DELAY RELEASE DEVICE

(75) Inventor: Abdul Rashid, Glasgow (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 08/356,635

(22) Filed: Dec. 15, 1994

Related U.S. Application Data

(63) Continuation of application No. 08/148,424, filed on Nov. 8, 1993, now abandoned, which is a continuation of application No. 07/743,403, filed on Aug. 14, 1991, now abandoned.

(30) Foreign Application Priority Data

Feb. 16, 1989 (GB) .................................................. 8903564
Feb. 15, 1990 (WO) ................................... PCT/GB90/00250

(51) Int. Cl.⁷ .............................. A61K 9/52; A61K 9/22
(52) U.S. Cl. ......................... 424/451; 424/422; 424/457; 424/463; 424/487; 424/488
(58) Field of Search ..................................... 424/453, 422, 424/484, 457, 463, 487, 488, 451

(56) References Cited

U.S. PATENT DOCUMENTS

| | | |
|---|---|---|
| 3,952,741 * | 4/1976 | Baker . |
| 4,327,725 * | 5/1982 | Cortese et al. . |
| 4,663,148 * | 5/1987 | Eckenhoff et al. . |
| 4,774,092 * | 9/1988 | Hamilton . |
| 5,023,088 * | 6/1991 | Wong et al. . |
| 5,059,423 * | 10/1991 | Magruder . |
| 5,110,597 * | 5/1992 | Wong et al. . |
| 5,387,421 * | 2/1995 | Amidon et al. . |

FOREIGN PATENT DOCUMENTS

| | | | |
|---|---|---|---|
| 132384 | * | 1/1985 | (EP) . |
| 0436236 | * | 11/1935 | (GB) . |
| 2206046 | * | 12/1988 | (GB) . |

* cited by examiner

*Primary Examiner*—Raj Bawa
(74) *Attorney, Agent, or Firm*—Nixon & Vanderhye

(57) ABSTRACT

Novel devices for the controlled release of active materials especially pharmaceuticals comprise a capsule formed from two separable pieces at least part of the capsule walls is water permeable. The capsule contains a water sensitive material which on contact with water causes the two pieces to separate. In the preferred embodiment the devices comprise a generally cylindrical tube closed at one or both ends by a water swellable plug. The devices find particular application as oral dosage forms for use in man.

29 Claims, 4 Drawing Sheets

CONTROLLED DELAY RELEASE DEVICE

This is a Rule 60 continuation of application Ser. No. 08/148,424, filed Nov. 8, 1993, now abandoned, which is a continuation of application Ser. No. 07/743,403, filed Aug. 14, 1991, now abandoned.

This invention relates to novel devices for the controlled release of active materials, especially pharmaceutical drugs to an aqueous medium. More particularly this invention relates to devices which are adapted to release their contents over a relatively short period following a controlled delay after administration—a pulsed release device.

BACKGROUND OF THE INVENTION

A wide variety of devices for the controlled release of drugs have been proposed. These dosage forms which may be termed "sustained release", "timed release", "prolonged release" or "controlled release" forms are designed to dispense the drug in a controlled reproducible manner. Previous attempts to provide release in a short burst over a period of the order of minutes e.g. those described in U.S. Pat. No. 3,952,741 have not been successful in controlling the delay before which the pulsed release of active material occurs.

DESCRIPTION OF THE INVENTION

He have now discovered a novel device which provides a sharp pulsed release after a predetermined reproducible delay following administration. Furthermore in a preferred embodiment the devices of this invention combine or utilise this release profile with the controlled release of active material over the period before and/or after the sharp pulsed release.

From one aspect our invention provides a controlled release device comprising a water permeable capsule containing at least one active material which is characterised in that the wall of said capsule is formed from at least two separable pieces and said capsule contains a water sensitive material which when wet will cause a positive pressure to be exerted on the interior wall of the capsule and result in the separation of the two pieces.

The capsule may be formed in any convenient shape for example spheroidal, ellipsoidal or cylindrical. Capsules which are generally cylindrical are preferred.

The walls of the capsule may be formed from any material which is biologically and medically compatible, non allergenic, insoluble in and non-irritating to body fluids and tissues. In the preferred embodiment at least a part of the wall is formed from a water permeable material.

In a preferred embodiment a first piece of the wall of the capsule defines at least one orifice which orifice is closed by a second separable piece which Is a plug. The first piece may take the form of a generally cylindrical tube closed at one end and open at the other, the open end defining an orifice.

In another embodiment a first piece of the wall defines more than one and preferably two orifices. A suitable first piece is a generally cylindrical open ended tube wherein each end of the tube may be regarded as defining an orifice. The two orifices may be closed by suitable plugs thus defining a capsule.

The walls of the capsules may be formed in part from a water impermeable material or materials. They may be of uniform or laminar construction. They may take the form of an impermeable coating applied to the surface of a water permeable material from a water impermeable material or materials. Indeed such a construction represents a preferred embodiment since it facilitates the control of the rate of ingress of water into the interior of the capsule.

The capsule is constructed in such a manner as to control the rate of ingress of water into the interior of the capsule. The rate of ingress is affected by the permeability of the material or materials from which the capsule is constructed, the thickness of the walls of the capsule and the surface area of the capsule. Altering the surface area of the water-permeable section of the capsule wall represents a convenient method of controlling the rate of ingress of water. The capsule is constructed and filled in such a manner as to control the delay following the initial exposure of the device after which the water sensitive material comes into contact with an aqueous medium. The length of the delay may be varied through a wide range. Delays of 0.5 hours may be useful in some applications, whereas delays of up to seven days may be useful in others. More usually the devices may be constructed so as to provide delay times of from 1 to 12 hours, more usually from 4 to 8 hours. Such devices are of particular value in oral dosage forms.

This control may be achieved in a variety of ways dependent upon the delay which is required. Where the second separable piece, i.e. the plug is of such a size and constructed of such a material that the flux of water through the plug alone is sufficient then the first separable piece, i.e. the walls may be and preferably is constructed from a water impermeable material such as a plastic. Where a greater influx of water is desired the walls of the capsule may be constructed entirely from a water permeable material or materials. Where the walls of the capsule define an orifice which is closed with a plug the closure should be substantially watertight. The plug may be formed from a water swellable material so that in use the swelling may contribute to the separation of the plug and will assist in retaining a water tight seal.

It will be appreciated from the above that there are a number of factors which affect the length of the delay between the initial exposure of the device to an aqueous medium and the release of the active material. The dimensions of the plug may be used to vary the delay time. The plug is preferably cylindrical but may adopt other geometries such as cone sections. In particular in the preferred embodiment utilising a cylindrical plug the delay is proportional to the length of the plug. The position of any plug may also be utilised to regulate the delay time. In particular where the outer surface of the plug is recessed so as to lie below the level of the mouth of the orifice the ejection of the plug will be delayed by a time which is a function of the depth of the recess. In a preferred form the device is preferably constructed so as to facilitate the positioning of the plug by the provision of a retaining means, e.g. a ridge or ledge on the interior face of the orifice at an appropriate depth. The plug is then inserted so as to engage this means which is sufficiently wide to prevent the plug penetrating to a greater depth. The nature of the materials used to construct the capsule and the thickness of those materials can all affect the length of this delay. The dimensions of the plug may vary according to the size and intended application of the device. For devices intended for use as oral dosage forms in man the plugs will typically have a length of from 1 to 5 mm. Where they are recessed so as to lie below the surface of the capsule, the recession will generally be no more than 3 mm and preferably no more than 2 mm. In practice the delay may be adjusted empirically for any particular device until the desired delay is achieved. It is a feature of the devices of the present invention that the delay times for particular devices are reproducible to a high level of accuracy.

The capsule preferably comprises only one orifice which extends from its exterior to its interior. The hollow capsule may be preformed and a hole subsequently drilled from the exterior into the hollow interior or alternatively the capsule may be formed with an orifice, e.g. by forming a cylinder around a rod. The capsule may be formed by coating a solution of a soluble polymer or an organosol onto a former, by compression or injection moulding of a suitable thermoplastic polymer, by powder compression or by direct reaction moulding. Capsules of particular utility in the devices of the present invention are those which take the form of a cylindrical capsule closed at one end and open at the other which may be formed by moulding a polymer around the ends of a rod or from extruded plastic tube cut into lengths and preferably sealed at one end.

The interior of the capsules of this invention contains at least one water sensitive component and at least one active material. The contents preferably fill the interior of the capsule and if necessary other materials such as inert excipient may be introduced. However in the preferred case the space available over and above that occupied by the active material will be filled with the water-sensitive component. The active material may be present as such or may be mixed with any excipient. It may also be present in a modified dosage form e.g. as a tablet or as coated material such as is described in our British Patent 2112730. These options enable the release profile of the device to be modified e.g. if particulate active material is employed it will be released as a single sharp pulse and where a modified dosage form is utilised that form will be released after the predetermined delay and the subsequent release profile will be that of the modified dosage form. A combination of these alternatives may be utilised to produce a device which provides a further novel release profile.

The device of the present invention may also be combined with another dosage form in a single capsule which will combine the release profile of the device of this invention with that of the other dosage form. Thus for example two separate devices of this invention designed to have different delay times before the release of the active material may be joined end to end so that the active materials are separated by an impermeable wall. Alternatively, a device of this invention may be joined to or combined with any other suitable controlled release device (of appropriate dimensions).

The water sensitive component may be a water swellable material or one which releases a gas on contact with water or an insert which expands on contact with water. The water sensitive material is preferably a water swellable material. The water swellable material is preferably a hydrogel. The hydrogel used is preferably one which is capable of swelling to at least 1.5 and more preferably at least 2.5 times its original volume by the absorption of water. The quantity of water-swellable material will preferably be at least sufficient that when fully swollen its volume will be greater than the interior volume of the capsule. There are a wide variety of natural and synthetic water swellable materials known in the art which may be utilised as the water sensitive component of the devices of this invention. Examples of such materials which are known to be useful in pharmaceutical and biomedical applications include poly N-vinylpyrrolidones; cross-linked cellulosic derivatives especially those known to be useful as tablet disintegrants; cross-linked dextrans especially those known to be useful for column separations and wound healing; cross-linked hydroxyethyl methacrylates especially those known to be useful in contact lenses; cross-linked gelatins and starches; hydrogels comprising cross-linked (meth)acrylic acid copolymers and their salts; cross-linked polyacrylamides and cross-linked poly (ethylene glycols). A preferred class of water swellable hydrogels are those which are derived from a homo- or co-poly(alkylene oxide) especially poly(ethylene oxide) cross linked by reaction with isocyanate or unsaturated ether groups. The water sensitive material may conveniently be utilised in the form of a crystalline or an amorphous powder wherein the size of the powder particles is such as to permit them to be easily packed into the capsule. Alternatively, the water sensitive material may be utilised in the form of a preformed monolith shaped so as to be readily inserted into the capsule. In the preferred embodiment such a monolith may take the form of a rod, bar or coil shaped so that its longitudinal axis lies along the longitudinal axis of a cylindrical capsule. Preferably the insert has the same cross section as the capsule and when wet extends in the longitudinal direction thus exerting pressure upon the end walls of the capsule. The separation of the capsule must be sufficient to permit ready access of the surrounding medium to the interior. However, for reasons of convenience, the pieces may be retained adjacent to one another by the provision of one or more members which link the separate pieces.

It will be appreciated that the devices find particular use in the administration of a pulse of active material after a controlled delay. The adaptability of the system enables it to be useful in a variety of applications.

The devices of this invention find wide application in medical and surgical, including veterinary, contexts and in horticulture and agriculture as well as outside these areas.

Specific classes of drug which may be utilised in a device of the invention include hypnotics, sedatives, tranquilisers, anti-pyretics, anti-inflammatory agents, anti-histamines, anti-tussives, anti-convulsants, anti-asthmatics, muscle relaxants, anti-tumour agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, β blockers such as atenolol and metoprolol; calcium antagonists such as nifedipine and nitrendipine, ACE inhibitors such as enalapril and captopril; $\beta_2$ agonists such as salbutamol and terbutaline; preparations containing various substances for the treatment of infection by pathogens including anti-fungal agents, for example metronidazole, anti-parasitic agents and other anti-microbials, anti-malarials, cardiovascular agents, preparations containing hormones, for example androgenic, estrogenic and progestational hormones, notably steroids such as oestradiol, sympathomimetic agents, hypoglycaemic agents, contraceptives, nutritional agents, peptides and proteins, nitrates such as isorbide dinitrate, mononitrate and GTN; xanthines such as theophylline; NSAID's such as piroxicam and diclofenac, benzodiazepines such as triazolam and zopiclone; α blockers such as prazosine and alfuzosine; antivirals such as acyclovir, zidovudine and ampligen, cephalosporins such as cefaclor; anti-spasmodics such as alverine and salicylates such as 5 amino salicylic acid; preparations containing enzymes of various types of activity, for example chymotrypsin, preparations containing analgesics, for example aspirin, and agents with many other types of action including nematocides and other agents of veterinary application. Mixtures of active substances may be incorporated into the device.

The devices of this invention are also useful in the treatment of diabetes and pernicious anaemia where, for example, the controlled release of insulin and cobalamin, respectively, may be utilised.

Moreover, the devices of this invention are suited to treatment, both prophylactic and therapeutic, of tropical diseases; for example malaria, leprosy, schistosomiasis and clonorchiasis. Examples of drugs which can be used as biologically active substance in pulsed release devices of this invention for the treatment of these and other tropical diseases include quinine, sulphonamides, rifamycin, clofazimine, thiambutasine, chlorphenyl derivatives, chlorguamide, cycloguanil, pyrimethamine, sulphadiazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

The release devices of this invention are also very well suited to veterinary applications. Examples include preparations of antibiotics for general antibacterial activity and also in the treatment of anaplasmosis in cattle; preparations for provision of a wide spectrum of activity against both ectoparasites, for example termites and endoparasites including arthropods, arrested larvae stages of nematodes, lungworms and general strongyles: these may comprise avermectins; preparations for provision of activity against tremotode, cestode and roundworm infections: these may comprise amoscanate and praziquantel: preparations for provision of activity against the ileria in cattle: these may comprise biologically active naphthoquinones such as menoctone; preparations for provision of activity against babesiosis in cattle, horses and dogs: these may comprise berenil, amidocarb and diampron; preparation for provision of activity against liver fluke in sheep and cattle and against Haemonchus species: these may comprise closantel. The devices according to this invention may have a wide variety of shapes and sizes according to their proposed application. They find particular application as oral dosage forms in which event they will typically have external dimensions corresponding to those of known oral dosage forms, e.g. capsules having sizes in the range triple zero to zero and from 1 to 8. Typically the length of a cylindrical capsule of this invention will be in the range 5 to 100 mm preferably 10 to 30 mm and the external diameter will be in the range 1 mm to 20 mm. In another embodiment the devices of this invention may be significantly smaller so as to facilitate the inclusion of a plurality of devices in a single dosage form, e.g. a conventional gelatin capsule. This enables different release profiles to be obtained. The devices may also find use in the various cavities of the body such as the buccal, peritoneal, interurterine and nasal cavities in which case they will be appropriately shaped and dimensioned. They may also be useful in similar applications in animals and may be dimensioned according to the requirements of these applications.

In order to ensure that the active material (either as such or in a modified dosage form) is released rapidly it is preferred to pack the device in such a way that the active material is adjacent to the point at which the walls of the capsule will separate. This ensures that the active material is rapidly expelled from the capsule when the two pieces separate. A further preferred embodiment of this invention comprises devices which are coated with an enteric coating so as to pass through the stomach and release the active material in the intestine. Such devices can be designed to release the active material a set period after the devices pass out of the stomach. They may be designed to release the active material in the colon. Any conventional enteric coating agent may be employed, for example cellulose acetate phthalate, polyvinylacetate phthalate hydroxypropylmethylcellulose phthalate and pH sensitive polyacrylate and polymethacrylate derivates.

The walls of the capsule may be formed from a wide variety of materials. Thus for example one embodiment of a device according to this invention comprises a capsule both pieces of which are formed entirely from water permeable material and which has a coating of impermeable material applied to a part of its exterior surface. The permeability of the walls of the capsules may also be modified by drilling a hole or a plurality of holes through a water impermeable section of the wall. Such holes may extend from the exterior to the interior of the capsule or simply through the impermeable part of a laminated or coated material. The size and the number of such holes will be such as to facilitate the controlled ingress of water into the interior of the capsule.

The term water permeable material includes all those materials which permit the passage of water from the exterior to the interior of the capsule. Thus semi-permeable and porous materials may be utilised. The materials will be selected so as to maintain their integrity at least until such time as the pieces of the capsule separate and to permit the controlled ingress of water. Examples of suitable materials include cellulosic derivatives such as cellulose acetate, cellulose nitrate and ethyl cellulose supported on or in the form of blends with water soluble polymers (excipients), e.g. substituted derivatives like HPMCs and HPECs. Other water soluble materials known in the art including polyethylene glycols of high molecular weight can also be blended with water impermeable materials to achieve the desired degree of permeability, e.g. blends of HPMC with cellulose acetate propionate and starch with polyvinyl chloride.

A preferred class of hydrophilic materials from which the capsules may be constructed are hydrogels and in particular a crosslinked hydrophilic polymer comprising polyethylene oxide residues, which polymer contains crystalline regions and has a crystalline melting temperature (Tm) of −10° C. to +70° C. Chemical crosslinking may be effected in a manner known per se. Where the hydrophilic polymer comprises functional groups which comprise an active hydrogen atom. Chemical crosslinking may be effected by means of a di- or poly-isocyanate (such as bis-(4-isocyanatophenyl)methane or bis-(4-isocyanato cyclohexyl) methane or a di- or poly -linear or cyclic olefinically unsaturated ether (such as acrolein tetramer); for example, as disclosed in our British 20470938, 2047094B and 2108517B, from which it will be apparent that where a diisocyanate or di-olefinically unsaturated ether is used a reactant comprising at least three active hydrogen atoms must also be present to ensure chemical crosslinking.

Entanglement crosslinking may be utilised, especially where the hydrophilic polymer has a high (for example, $\overline{M}n$ greater than 100,000) molecular weight, by chemically crosslinking, in intimate admixture with the hydrophilic polymer, at least one monomer of functionality greater than two. Examples of such monomer include di- and poly-olefinically unsaturated hydrocarbons, such as divinyl benzene, and di- and poly-olefinically unsaturated esters or ethers, such as acrolein tetramer, triallyl cyanurate or glycol dimethacrylate.

Preferred hydrophilic polymers comprising polyethylene oxide residues have a number average molecular weight, $\overline{Mn}$, of the polyethylene oxide greater than 1,500, preferably greater than 3,000; for example, from 4,000 to 12,000 or higher.

The hydrophilic polymer may be a homopolymer or a random, alternating or block copolymer, especially a homopolymer or a random or block copolymer of ethylene oxide with, for example, a homologue such as propylene oxide. The permeability and the swellability of these particular preferred hydrogels may be varied by varying the proportions of the hydrophillic polymer crosslinking agent (and where appropriate the reactant having at least three active hydrogen atoms). In a preferred embodiment the two separable pieces of the capsule will be constructed from two different hydrogels. In the preferred devices the plug will preferably be constructed from a hydrogel having a higher degree of swelling than that used to form the walls of the cylinder. These preferred hydrogels may also be employed as the water swellable material which is contained within the capsule. Those hydrogels which exhibit a higher degree of swelling are preferably used for this purpose. They may readily be prepared in the form of moulded monoliths or in particulate form. In the preferred devices the water swellable material and the plug may be constructed from the same material.

The hydrophilic polymer, for example, polyethylene oxide, may also be foamed in a manner known per se. For example, the polyethylene oxide may be chemically crosslinked by means of a di- or poly-isocyanate in the presence of water; the polyethylene oxide may also be foamed by the direct injection of a pneumatogen, such as a fluorocarbon; for example, fluorotrichloromethane (e.g. "ARCTON" ex ICI Ltd: "ARCTON" is a registered Trademark).

Examples of suitable materials which may be used to coat the surface of the capsule include nitrocellulose, cellulose esters, ethers and acetals, polymethacrylate copolymers, polyurethanes, air curing coatings such as alkyd resins and moisture curing coatings such as polyurethanes containing an excess of isocyanate groups.

Examples of hydrophobic materials which may be used in the construction of the walls of the capsule include polyethylene, polypropylene, polymethylmethacrylate, polyvinyl chloride, polystyrene, polyurethanes, polytetrafluoroethylene, nylons, polyformaldehydes, polyesters, cellulose acetate and nitrocellulose. A further class of materials which can advantageously be utilised in the construction of the devices of this invention are biodegradable materials provided they retain their structural integrity in the environment of use at least until after the separation of the two portions of the capsule.

EXAMPLES AND BRIEF DESCRIPTION OF THE DRAWINGS

The invention is illustrated by the following examples with reference to the accompanying drawings, in which.

EXAMPLE 1

Figure 1:
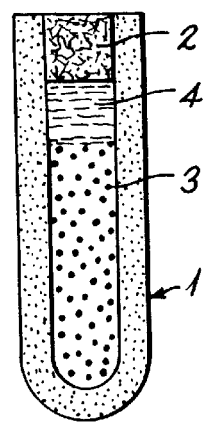
FIG. 1 is a schematic representation of a device of the invention.

A device having the configuration shown in FIG. 1 was prepared using the following materials.

FIG. 1 is a diagrammatic representation of a section through the longitudinal axis of a device of this invention. The device comprises a hydrogel cylinder (1) which is closed with a cylindrical plug (2). The interior of the cylinder is filled with a water swellable material (3) and an active material (4).

The cylinder had an external diameter of 6 mm and a length of 17 mm. Its internal diameter was 3 mm. The plug had a diameter of 3 mm and a length of 3 mm.

The hydrogel cylinder was prepared by batch polymerising 5.5 parts of Desmodur W [a proprietary bis-(4-isocyanatocyclohexyl) methane product] with 3 parts of hexane triol (HT) and 1 part of a polyethylene glycol (PEG) having Mn 3830 using ferric chloride as the catalyst. The polymerisation was carried out in a suitable mould into which a former was inserted so as to form the hollow cylinders.

The plug was prepared in a similar manner from 2.8 parts of Desmodur W, 1.2 parts HT and 1 part PEG of Mn 8660 the polymerisation being carried out within a length of silicone tubing of appropriate internal diameter so as to form a rod of the hydrogel. The rod was then cut to length.

The hydrogel granules were prepared from 2.8 parts of Desmodur W, 1.2 parts HT and 1 part PEG Mn 8660 formed into billets which were cut into small pieces, swollen in water, liquidised, homogenised, filtered, washed with boiling water, refiltered and dried.

The device was assembled and tested using salbutamol sulphate as the drug. 60 mg of the hydrogel granules (500–700 microns) were accurately weighed directly into the hollow cylinder and compacted with a hydrogel rod. About 8 mg of salbutamol sulphate was accurately weighed into the cavity on top of the granules. The plug was introduced so as to block the end of the cylinder.

Figure 2:
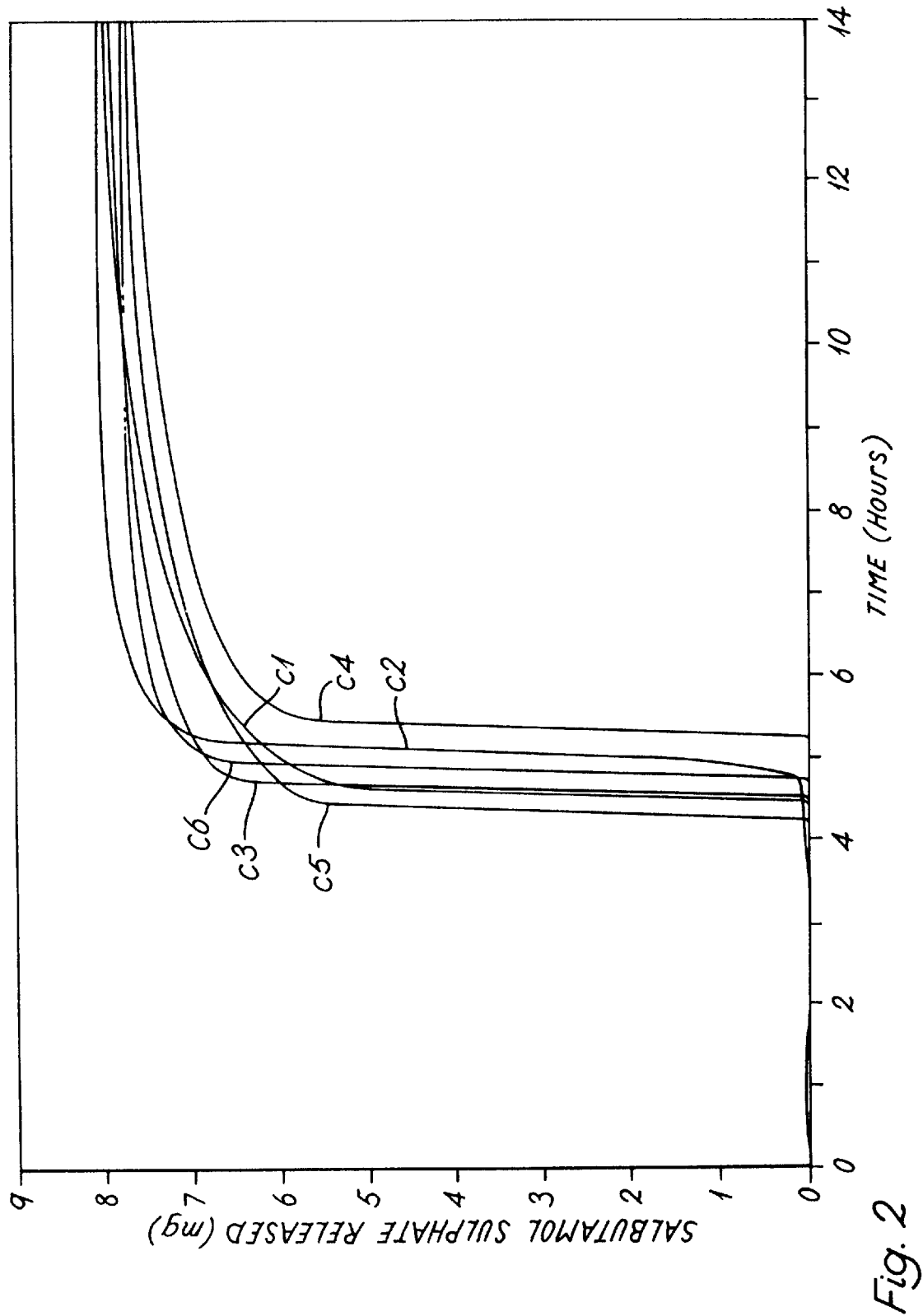

The release profile of six of these devices in vitro was tested in water at 37° C. using a U.S. Pharmcopoeia dissolution bath and is shown graphically as FIG. 2.

Figure 3:
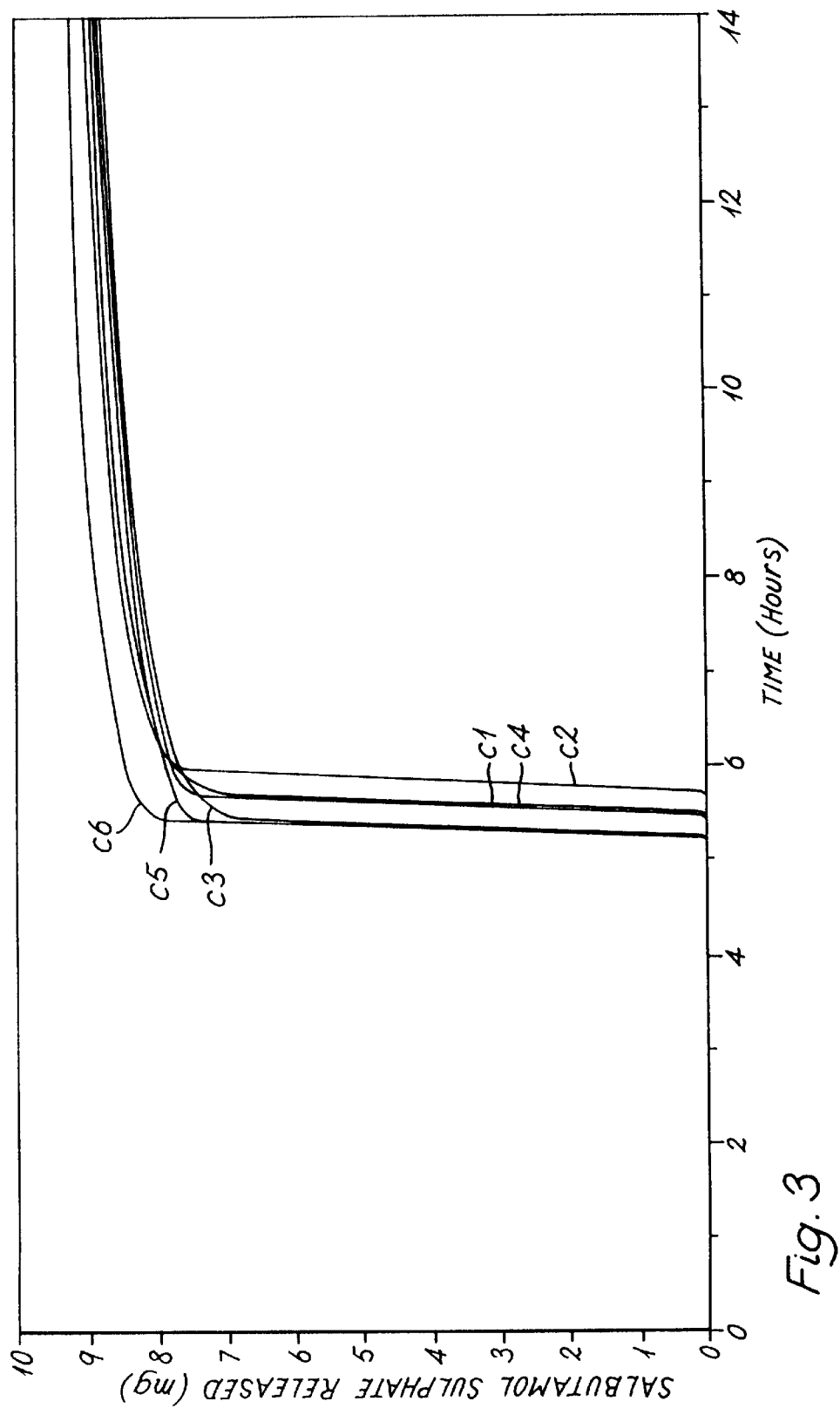

Six identical devices were prepared except that the plug was inserted so as to be recessed to a depth of 0.5 mm below the outer surface of the wall of the capsule. The release profile of these devices is shown graphically as FIG. 3.

EXAMPLE 2

Figure 4:
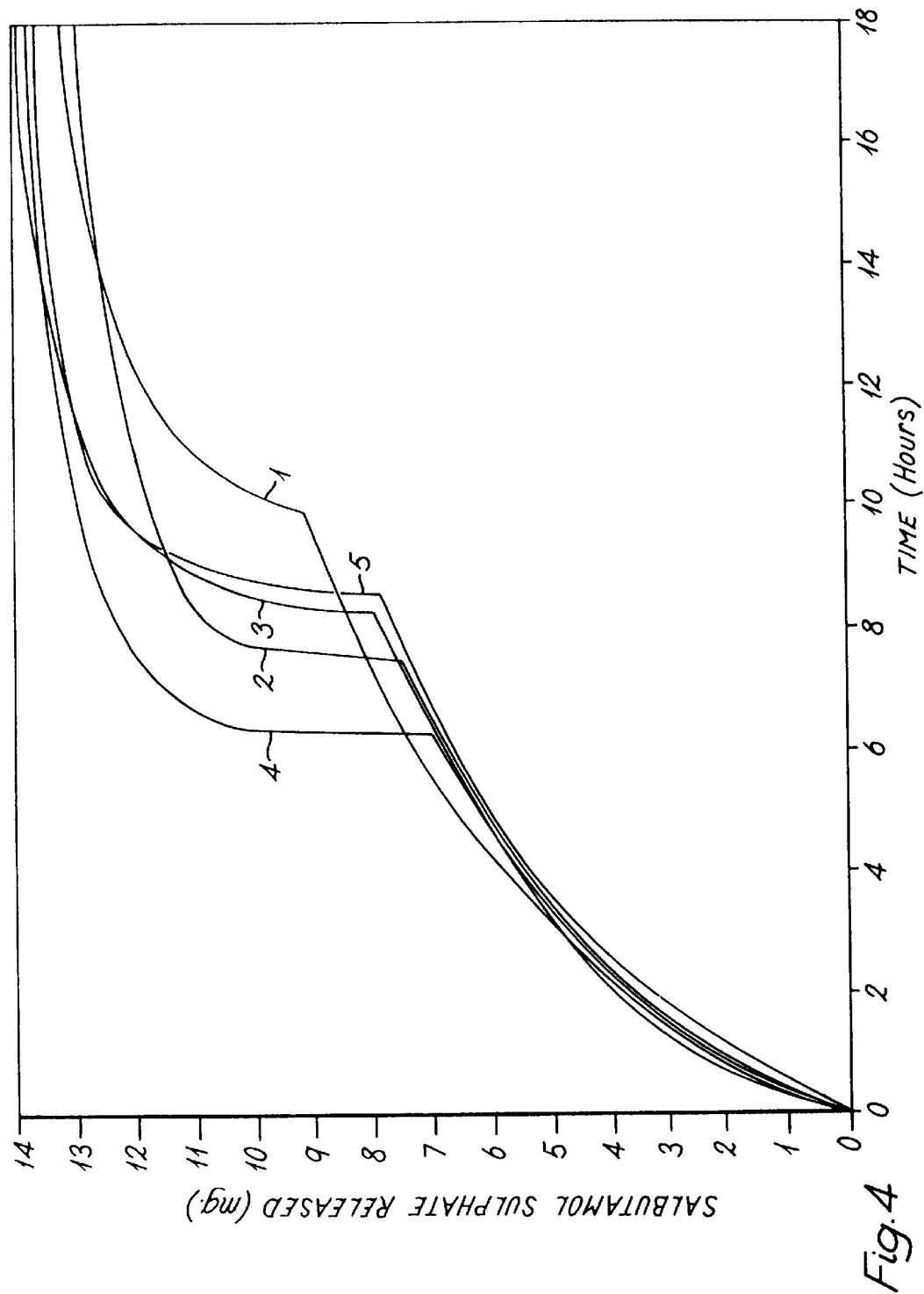

Devices useful in the controlled release of salbutamol sulphate were prepared in an identical manner to that described in Example 1 except that the hollow hydrogel cylinders were first immersed for 24 hours in a solution of 1600 mg of salbutamol sulphate in 60 cc of a 50:50 ethanol/water mixture. Thereafter the cylinders were dried to a constant weight. These devices were charged using the above technique with 6 mg of salbutamol sulphate crystals. The release profile of these devices was determined and is shown as FIG. 4.

EXAMPLE 4

Figure 5:
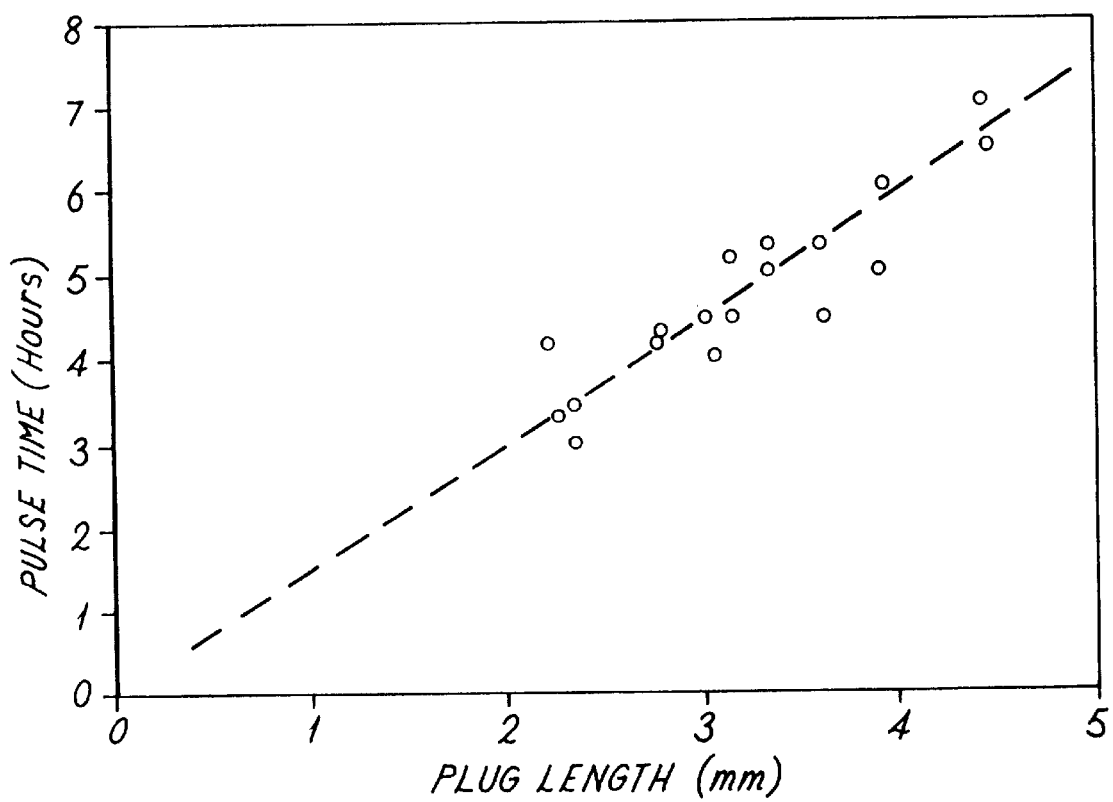
FIGS. 2–5 are graphs showing release profiles of devices prepared as described in Examples 1–5.

A series of devices having the general configuration shown in FIG. 1 were prepared in which the hollow cylinder was of identical composition and size as that of Example 1. The hydrogel used to form the plug was of identical composition but the length of plug was varied between 2 and 5 mm. The plug was positioned so that its outer surface was flush with the outer surface of the cylinder. The release profile of the devices was measured and the pulse time, i.e. the time at which amount of drug released rapidly increased was recorded. The relationship between the pulse time and the length of the plug is presented graphically as FIG. 5.

EXAMPLE 5

A series of devices having the general configuration as shown in FIG. 1. The hollow cylinder was of identical composition and size as that of Example 1. Hydrogel rods having the same composition as the plug of Example 1 were prepared and cut to length as necessary. In these examples the hydrogel powder was replaced by a rod of the hydrogel (being the same material which was used to form the plug). The length of the rod varied as shown in the data in Table 1 below.

TABLE 1

| Capsule Length (mm) | Plug Length (mm) | Plug Diameter (mm) | Rod Length (mm) | Rod Diameter (mm) | Recession (mm) |
| --- | --- | --- | --- | --- | --- |
| 17.5 | 3.0 | 3.4 | 9.75 | 3.4 | 0.5 |
| 17.5 | 3.0 | 3.4 | 8.5 | 3.0 | 0.5 |
| 17.5 | 3.0 | 3.4 | 7.5 | 3.0 | 0.5 |

The release profile of all these devices was measured and the pulse time recorded. The average pulse time for nine devices of each plug length, the standard deviation from that time and the 95% confidence pulse interval are shown in the following Table.

| Rod Length (mm) | Average Pulse (hours) | Standard Deviation | 95% Confidence Interval (hours) |
| --- | --- | --- | --- |
| 9.75 | 4.34 | 0.33 | 3.60–5.02 |
| 8.50 | 6.74 | 0.32 | 6.10–7.37 |
| 7.50 | 8.28 | 0.37 | 7.53–9.02 |

What is claimed is:

1. A controlled release device for oral administration to a human patient, the device being effective to pass through the patient's stomach into the intestine thereby to deliver an active agent thereto, the device containing a single therapeutic dose comprising at least one active agent and a water permeable capsule coated with an enteric coating effective to prevent the ingress of liquid from the stomach into said capsule during the passage thereof through the stomach into the intestine, said capsule including a cavity suitable to receive said at least one active agent; an interior wall defining an orifice, said orifice being in communication with said cavity; a closure member that is separably engageable with said capsule to close said orifice, said orifice being in communication with said cavity; and a water sensitive material that is receivable by said cavity, wherein upon the passage of the device from the stomach into the intestine, said water sensitive material expands and causes an increasing positive pressure to be exerted on said interior wall of said capsule thereby to effect the rapid separation of said closure member from said capsule and the release of substantially all of the active agent therefrom in a single pulse.

2. A device according to claim 1, in which said closure member forms a substantially watertight seal with said orifice.

3. A device according to claim 1, in which release of said active agent occurs after a controlled delay after the device has left the stomach.

4. A device according to claim 1, in which said closure member is a plug.

5. A device according to claim 1, in which said capsule is a cylindrical tube which is closed at one end and open at the other end.

6. A device according to claim 4, in which said plug is a cylindrical plug.

7. A device according to claim 4, wherein a retaining means is provided on said interior wall of said capsule which engages said plug.

8. A device according to claim 1, wherein said water-sensitive material is a water-swellable material.

9. A device according to claim 8, wherein said water-swellable material is selected from the group consisting of poly-N-vinyl pyrrolidones, cross-linked cellulosic derivatives, cross-linked dextrans, cross-linked hydroxyethyl methacrylate, cross-linked gelatins and starches, cross-linked (meth)acrylic acid copolymer hydrogels, cross-linked polyacrylamide hydrogels and cross-linked polyethylene glycol hydrogels.

10. A device according to claim 8, wherein said water swellable material is a hydrogel.

11. A device according to claim 8, wherein said water-swellable material is capable of swelling to at least 1.5 times its original volume by absorption of water.

12. A device according to claim 8, wherein said water-swellable material is a hydrogel derived from a homo- or co-poly(alkylene oxide) cross-linked by reaction with isocyanate or unsaturated ether groups.

13. A device according to claim 8, wherein said water-swellable material is a particulate solid.

14. A device according to claim 8, wherein said water-swellable material releases a gas upon contact with water.

15. A device according to claim 1, wherein said water-sensitive material is a preformed monolith.

16. A device according to claim 15, wherein said monolith takes the form of a rod, bar or coil adapted so that when inserted into said capsule its longitudinal axis lies along the longitudinal axis of said capsule.

17. A device according to claim 1, wherein said at least one active agent is a particulate solid.

18. A device according to claim 1, wherein said capsule contains said active agent in a dosage form.

19. A device according to claim 1, wherein the active agent is positioned adjacent to a point at which said capsule and said closure member will separate.

20. A device according to claim 1, wherein said interior wall defining said orifice is impermeable to water.

21. A device according to claim 1, wherein said interior wall defining said orifice is formed from a hydrophobic material selected from the group consisting of polyethylene, polypropylene, polymethyl methacrylate, polyvinyl chloride, polystyrene, polyurethanes, polytetrafluoroethylene, nylons, polyformaldehydes, polyesters, cellulose acetate and nitrocellulose.

22. A device according to claim 1, wherein said interior wall defining said orifice is water permeable.

23. A device according to claim 22, wherein said interior wall defining said orifice is formed from a hydrogel.

24. A device according to claim 23, wherein said interior wall defining said orifice is formed from a hydrogel derived from a homo-or co-poly(alkylene oxide) cross-linked by reaction with isocyanate or unsaturated cyclic ether groups.

25. A device according to claim 1, wherein said closure member is water swellable.

26. A device according to claim 25, wherein said closure member is formed from a hydrogel.

27. A device according to claim 26, wherein said closure member is constructed from a hydrogel derived from a homo-or co-poly(alkylene oxide) cross-linked by reaction with isocyanate or unsaturated cyclic ether groups.

28. A device according to claim 1, wherein said capsule has a length of from 10 to 30 mm and an external diameter of from 1 to 20 mm.

29. A method of preparing a controlled release device for human oral administration comprising a capsule containing an active agent, said capsule including a cavity suitable to receive said active agent; an interior wall defining an orifice, said orifice being in communication with said cavity; a closure member that is separably engageable with said capsule to close said orifice; and a water sensitive material that is receivable into said cavity, wherein upon the passage of the device from the stomach into the intestine said water sensitive material expands and causes an increasing positive pressure to be exerted on said interior wall of said capsule, thereby to effect the rapid separation of said closure member from said capsule and the release of substantially all the active agent therefrom in a single pulse, said method comprising the steps of sequentially inserting a said water-sensitive material and a said active agent respectively into said cavity defined by said capsule and said closure member; and closing said cavity with said closure member.

* * * * *